United States Patent [19]

Whitmore

[11] 4,144,749
[45] Mar. 20, 1979

[54] TOTAL BODY VOLUME METER

[76] Inventor: Henry B. Whitmore, Rte. 1, Box 369, San Antonio, Tex. 78211

[21] Appl. No.: 859,083

[22] Filed: Dec. 9, 1977

[51] Int. Cl.² ............................................. G01F 17/00
[52] U.S. Cl. ...................................................... 73/149
[58] Field of Search ................ 73/149, 290 B; 128/2.5

[56] References Cited

U.S. PATENT DOCUMENTS

| | | | |
|---|---|---|---|
| 1,901,687 | 3/1933 | Zook | 33/174 |
| 2,662,400 | 12/1953 | Weiner et al. | 73/149 |
| 2,706,908 | 4/1955 | MacRoberts | 73/149 |
| 3,113,448 | 12/1963 | Hardway et al. | 73/149 X |
| 3,769,834 | 11/1973 | Fletcher et al. | 73/149 |

FOREIGN PATENT DOCUMENTS 1480470  9/1967  France.
 210408  9/1968  U.S.S.R.

*Primary Examiner*—Donald Watkins
*Attorney, Agent, or Firm*—Gunn & Lee

[57] ABSTRACT

The present apparatus shows a device for measuring the total volume displaced by a human body. A tank portion has an enlarged upper opening for an individual to enter the tank therethrough. Thereafter, while the individual is in a sitting position inside of the tank, the enlarged upper opening is closed with the individual's head extending upward into an open ended cylinder. A tall cylinder of equal diameter with the open ended cylinder is connected to a control console which pumps the water level inside of the tank up to a predetermined point inside of the open ended cylinder. Thereafter, if the individual lowers his head below the water level by releasing a seat on which the individual is sitting, an accurate reading of the column of water displaced can be obtained on a manometer and compared with a prior reading before entering the tank. By determining the total volume of the columns of water displaced in the tall cylinder and the open ended cylinder, the total volume of water displaced by the individual can be accurately obtained.

14 Claims, 8 Drawing Figures

TOTAL BODY VOLUME METER

BACKGROUND OF THE INVENTION

The present invention relates to a total body volume measuring apparatus and, more particularly, to a total body volume measuring apparatus utilizing a tank portion and a console portion both having a uniform cross section column of water. An enlarged upper opening in the tank portion allows for removal of the individual in case of physical problems, and manometers provide for ease of determining the total volume displaced by the individual.

BRIEF DESCRIPTION OF THE PRIOR ART

Prior to the present invention, many different types of body volume measuring apparatuses have been utilized in the past. With recent programs in aerospace medicine and emphasis on physical fitness, it has become very important to know the total volume displaced by a human body. By knowing the volume displaced and the weight of the individual, physicians and/or therapists can determine with a fair degree of accuracy the muscle or fat content of the human body. Knowing the amount of fat content of the human body can be very important in the treatment of patients with cardiac problems. Also, knowing the weight displaced per unit volume is important when determining pay load of space vehicles.

U.S. Pat. No. 3,769,834 by Fletcher, which was assigned to the National Aeronautics and Space Administration, shows a system for measuring the volume of the human body and volume variations under 0 gravity conditions. The Fletcher invention, which is designed for the measurement of volume changes under 0 gravity, is not practical for use by individuals being treated by physicians or therapists. Normally, individuals being treated by physicians or therapists have particular problems that may be related to overweight conditions. The Fletcher invention in no way indicates the weight per unit volume of the body which would be important to a physician or therapist.

Zook (U.S. Pat. No. 1,901,687) shows a rather complicated apparatus for measuring the body volume, including a hoist for raising and lowering a platform inside of a tank. The apparatus as shown in Zock is very complicated, including gears and pulleys for raising and lowering the platform, graphs for simultaneously recording information, as well as numerous other accessories. However, the invention as shown in Zock does not provide for ease of removal of an individual in case of complications.

Another body measuring device for measuring the volume displaced by limbs is shown in French Pat. No. 1,480,470.

Other body measuring devices known to applicant include large vertical tanks wherein an individual is lowered into the tank. However, the accuracy of such large vertical tanks having a large cross-sectional area is considerably less than the present invention. Also, if for some reason the individual collapsed inside of the tank, it would be very difficult to remove the individual with the possibility of drowning being continuously present.

SUMMARY OF THE INVENTION

It is an object of the present invention to provide a simple total body volume measuring device that is accurate.

It is another object of the present invention to provide a tank in which an individual may enter through an enlarged upper opening and sit on a vertically moveable seat located therein. Thereafter, by the individual releasing the seat and lowering his head below the water, an accurate measurement of the total body volume displaced can be obtained.

The tank, which is designed for an individual to sit therein on a releasable and vertically moveable seat, has an enlarged upper opening through which an individual may enter the tank. Thereafter, a lid which has an open ended cylinder extending upwardly therefrom is sealed to the top of the tank. The tank is connected to a control console by means of a conduit. The console has a tall cylinder of equal diameter with the open ended cylinder for holding water therein. By closing the lid of the tank and pumping water from the tall cylinder until water begins to enter the open ended cylinder, a first measurement may be taken on a tank manometer and a control console manometer. The sum of the two manometer measurements are recorded. By pumping a portion of the water inside of the tank back into the tall cylinder, an individual may then enter the tank through the enlarged upper opening and sit on the releasable seat. After closing the lid so that the individual's head extends into the open ended cylinder, a portion of the water is then pumped from the tall cylinder back into the tank until the water level begins to rise inside of the open ended cylinder. By releasing the seat, the individual's head is lowered into the water, and the sum of the tank and control console manometers is recorded. After the individual emerges from below the water, the difference between the first sum and the second sum will give the height of the column of water displaced, which difference can be multiplied times the cross-sectional area of the cylinders to give the total volume displaced.

By appropriate valving, flow to or from the tank or the control console can be prevented when the pumps are not energized. Also, appropriate valving can maintain the reading in the manometer for an extended period of time, even though levels in either the tank or the control console have changed.

DESCRIPTION OF THE PREFERRED EMBODIMENT

Figure 1:
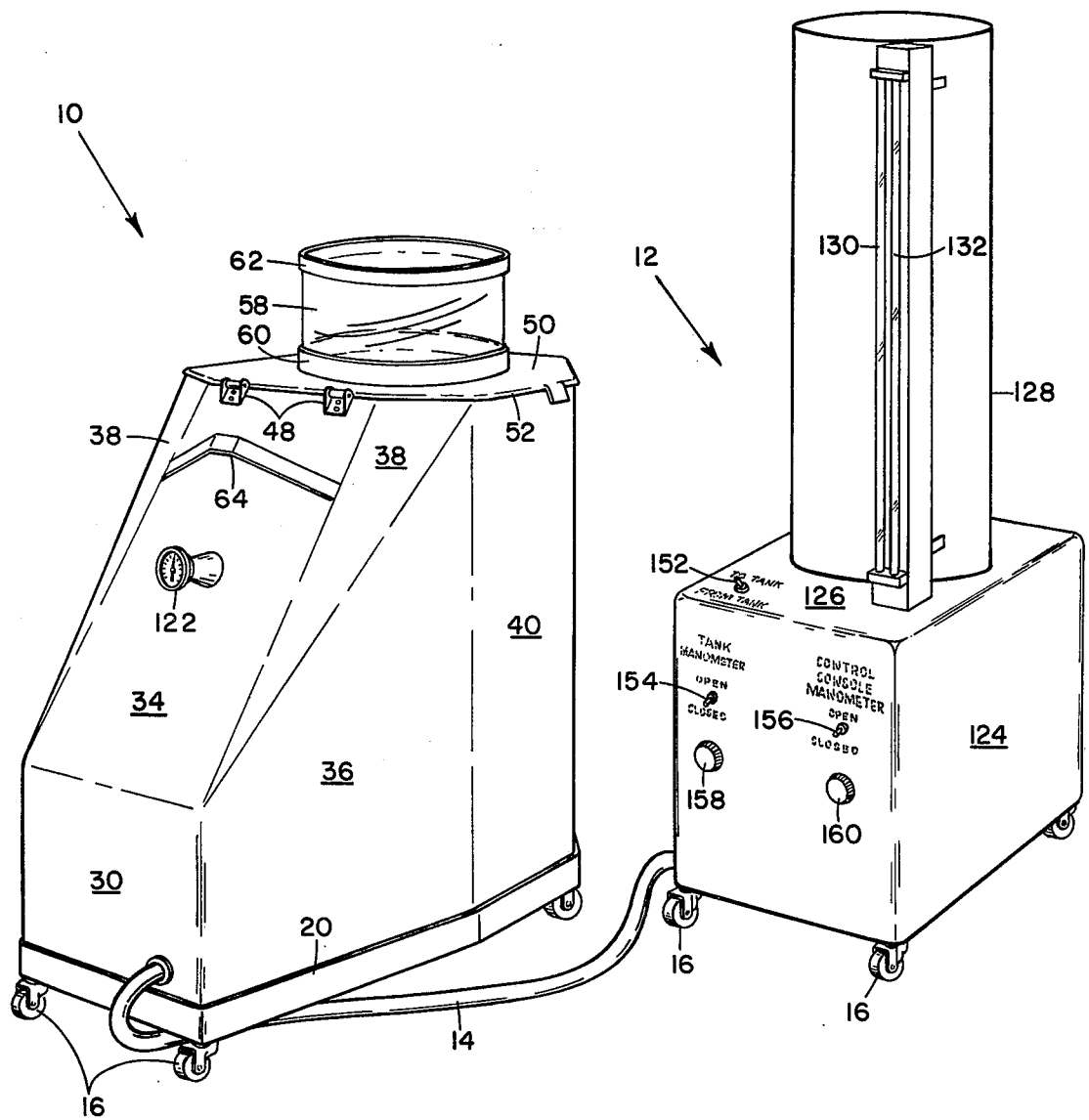
FIG. 1 is a pictorial view of a total body volume meter including tank and control console.

Referring now to FIG. 1 of the drawings, there is shown a pictorial view of the total body volume meter which includes a tank, represented generally by reference numeral 10, and a control console, represented generally by reference numeral 12. The control console 12 is connected to the tank 10 by means of flexible hose 14. A suitable source of electric power is normally connected to the control console 12. Both the tank 10 and the control console 12 may be located on rollers 16 for ease of movement.

Figure 7:
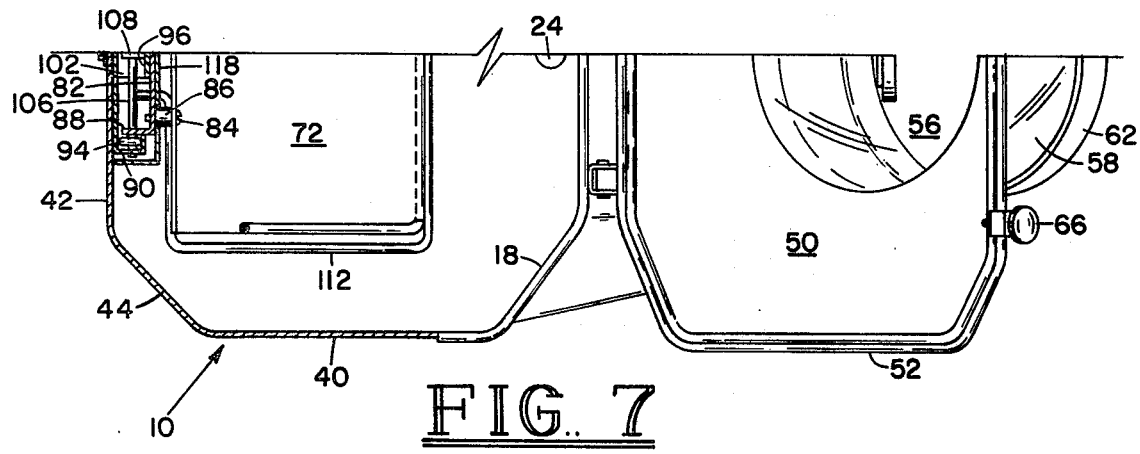
FIG. 7 is a partial sectional view of one-half of FIG. 2 taken along section lines 7—7.
Figure 2:
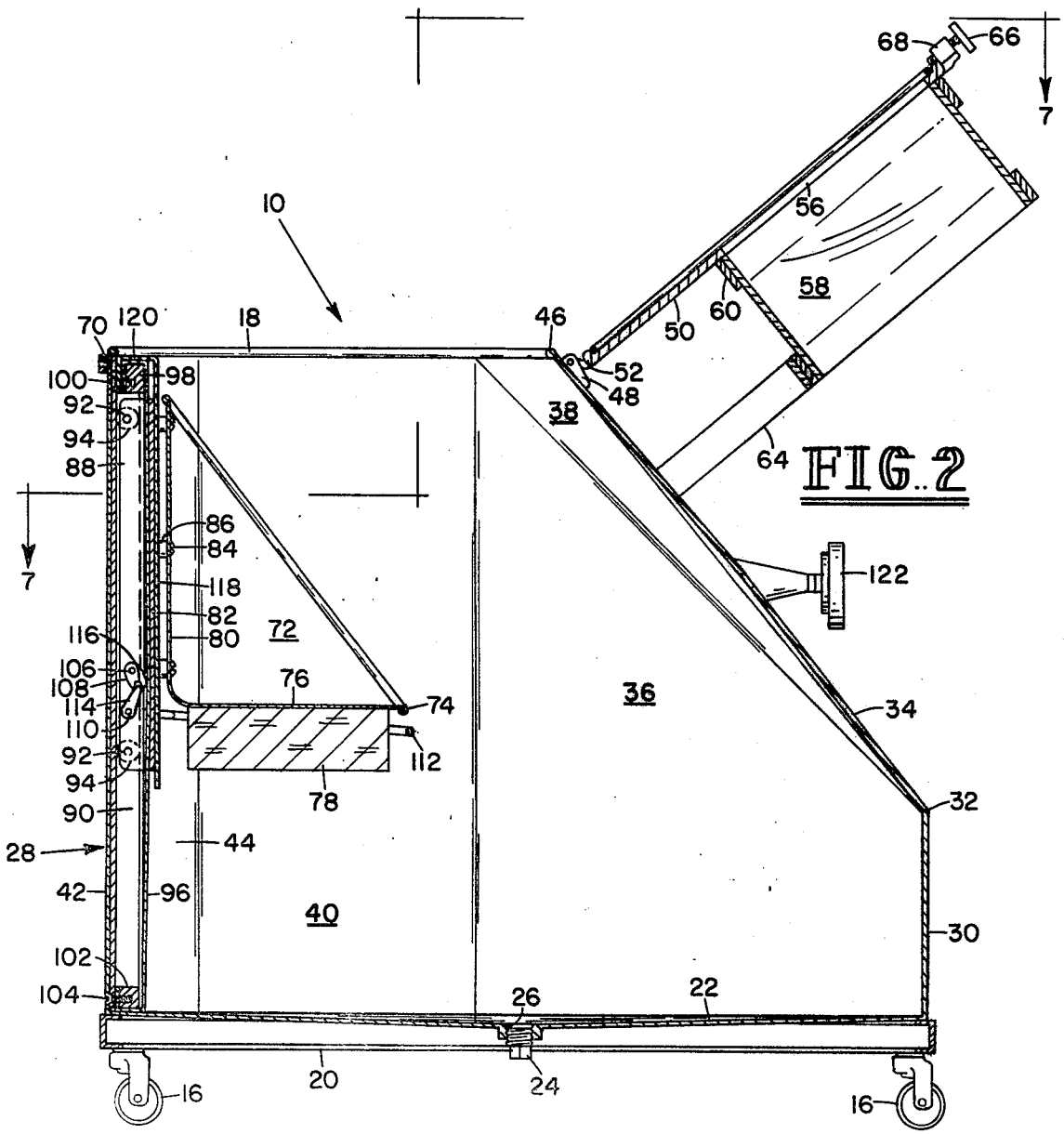
FIG. 2 is a cross-sectional view of the tank.

Referring specifically to the tank 10 as shown in FIG. 1 in conjunction with FIGS. 2 and 7, a better understanding of the tank can be obtained. The tank 10 rides on a lower support structure 20 that may be formed from any suitable substance, such as channeled stainless steel. The rollers 16, which are free to pivot, connect to the lower support structure 20. The body of the tank 10, which is secured to the lower support structure 20 by any suitable means such as welding, has a bottom 22 that slopes toward the center thereof where a drain plug 24 is located in threaded hole 26. By removal of the drain plug 24, or in the alternative by opening a valve (not shown), water contained inside of tank 10 can be completely removed. The flexible hose 14 may be connected via the threaded hole 26 that receives the drain plug 24 therein, or may be connected through the side of the tank 10 as shown in FIG. 1.

Extending upwardly from the bottom 22 are sides represented generally by reference numeral 28. The front side 30 has a bend 32 located therein to form a sloping upper front surface 34. To make the tank 10 smaller toward the front, forward side walls 36 taper inward. For aesthetic appeal and structural support, the connection between the forward side walls 36 and the sloping upper front surface 34 is made by angular surfaces 38. Rearward side walls 40 connect to the forward side walls 36 and extend from the bottom 22 to the enlarged upper opening 18. For aesthetic, sanitation and strength, the rearward side walls 40 are connected to the back 42 by corner panels 44 with the angle between the corner panels 44 and the sides 40 or back 42 being approximately 135°.

Each of the sides 28 just described in the preceding paragraph are formed together with the bottom 22 by conventional means, such as welding, bending or otherwise, to form a water tight container. The sides 28 terminate at the upper end thereof as enlarged upper opening 18. To give additional strength to the upper edge of sides 28, they may be rolled or formed in conjunction with rod 46 that encircles the enlarged upper opening 18.

Mounted on the sloping upper front surface 34 adjacent to enlarged upper opening 18 is a hinge 48. The hinge 48 connects to lid 50 used to cover the enlarged upper opening 18. The edges of the lid 50 have a lip 52 around the outer edges thereof that seal against the rod 46 by means of resilient material 54. Resilient material 54 may be made from any suitable substance, such as rubber. The resilient material 54 is connected to the lid 50 by any suitable means, such as bonding.

A circular hole 56 is formed in lid 50, which circular hole 56 is designed to receive a transparent plastic cylinder 58 contiguous therewith. The transparent plastic cylinder 58 is open ended and seals with the lid 50. The transparent plastic cylinder 58 is structurally supported by metal band 60 surrounding hole 56. The transparent plastic cylinder 58 extends upward from the lid 50 a predetermined distance normally between 1 and 2 feet. The uppermost portion of the transparent plastic cylinder 58 is surrounded by an upper metal band 62 to give it additional strength. To support the transparent plastic cylinder 58 when the lid 50 is in the open position, a bracket 64 extends upward from the sloping upper front surface 34, which bracket 64 is connected to the tank 10 by any suitable means, such as welding. By designing the bracket 64 so that it strikes the upper metal band 62, potential damage to the transparent plastic cylinder 58 can be minimized.

To hold the lid 50 in the closed position so that resilient material 54 will seal against the rod 46 encircling enlarged upper opening 18, hand screw 66 threadably extends through retaining block 68 attached to lid 50. After closing the lid 50, hand screw 66 is threadably connected with threaded block 70 which securely holds lid 50 in the closed position.

Referring now to the inside of tank 10, a seat 72 is located therein. The seat 72 is made from formed sheet metal and basically resembles a bucket seat with a support rod 74 encircling the front, bottom, sides and top of the seat 72 for additional strength. Attached to the bottom 76 of the seat 72 is a float 78 that is used to urge the seat 72 upward upon filling tank 10 with water. The back 80 of the seat 72 is connected to a seat carriage 82 by means of bolts 84 and spacers 86. The seat carriage 82 has a flange 88 on each end thereof that is received inside of channels 90. Pivotally connected to flanges 88 of seat carriage 82 by means of pins 92 are rollers 94. The rollers 94 are received inside of channels 90 secured to the back 42. Vertical movement of the seat 72 will also cause vertical movement of the seat carriage 82 and rollers 94 located inside of the vertical channels 90.

Inside of the seat carriage 82 and adjacent thereto is a strap 96 that may be made from nylon or any other suitable substance. The strap 96 is anchored by an upper retaining block 98 and screw 100, and lower retaining block 102 and screw 104. Screws 100 and 104 are secured to the back 42 of the tank 10. While the rollers 94 are pivotally connected toward the outside of flanges 88 of seat carriage 82, cam cross rod 106 extends internally between the flanges 88. Pivotally mounted on the center portion of the cam cross rod 106 is a cam 108. Also, a lever cross rod 110 connects internally between the respective flanges 88 of the seat carriage 82. A lever arm 112, which extends through a suitable slot opening (not shown) in the seat carriage 82, encircles the float 78 immediately below the seat 72. The lever arm 112 is rigidly connected to lever cross rod 110. By moving lever arm 112 up or down, lever cross rod 110 will cause linkage 114 rigidly connected thereto to rotate. One end of the linkage 114 is received in notch 116 of cam 108; therefore, rotation of linkage 114 will also cause cam 108 to rotate.

If the seat 72 had weight applied thereto, the cam 108 would rub against strap 96 thereby pivoting on cam cross bar 106 toward strap 96 forcing the strap 97 against seat carriage 82. The forcing of the strap 96 against the seat carriage 82 by means of cam 108 acts as a brake to prevent downward movement of the seat 72. An individual sitting in seat 72 can pull upward on lever arm 112 thereby causing rotation of linkage 114. Linkage 114 in turn rotates cam 108 on cam cross rod 106 to remove the braking action of strap 96 against seat carriage 82 thereby allowing seat 72 to be lowered. To prevent an individual located in seat 72 from getting entangled in the rollers 94, a cover 118 extends downward from enlarged upper opening 18. Cover 118 is anchored by channel 120 which encircles upper retaining block 98. Appropriate slots (not shown) are contained in cover 118 to allow for vertical movement of bolts 84 and spacers 86, plus vertical movement of lever arm 112.

Located on the sloping upper front surface 34 is a thermometer 122 for measuring the temperature of the water inside of tank 10. For the most accurate measurements, the temperature of the water should be near body temperature.

Referring now to the control console 12, it has a lower control cabinet 124 as can be clearly seen in FIG.

1. Mounted on an upper surface 126 of the lower control cabinet 124 is a tall cylinder 128 which has the same diameter as transparent plastic cylinder 58. Connected to the tall cylinder 128 are manometers 130 and 132. Manometer 130 is connected through the control cabinet 124 to tall cylinder 128. Manometer 132 is connected through the control cabinet 124 to tank 10 via flexible hose 14.

Figure 8:
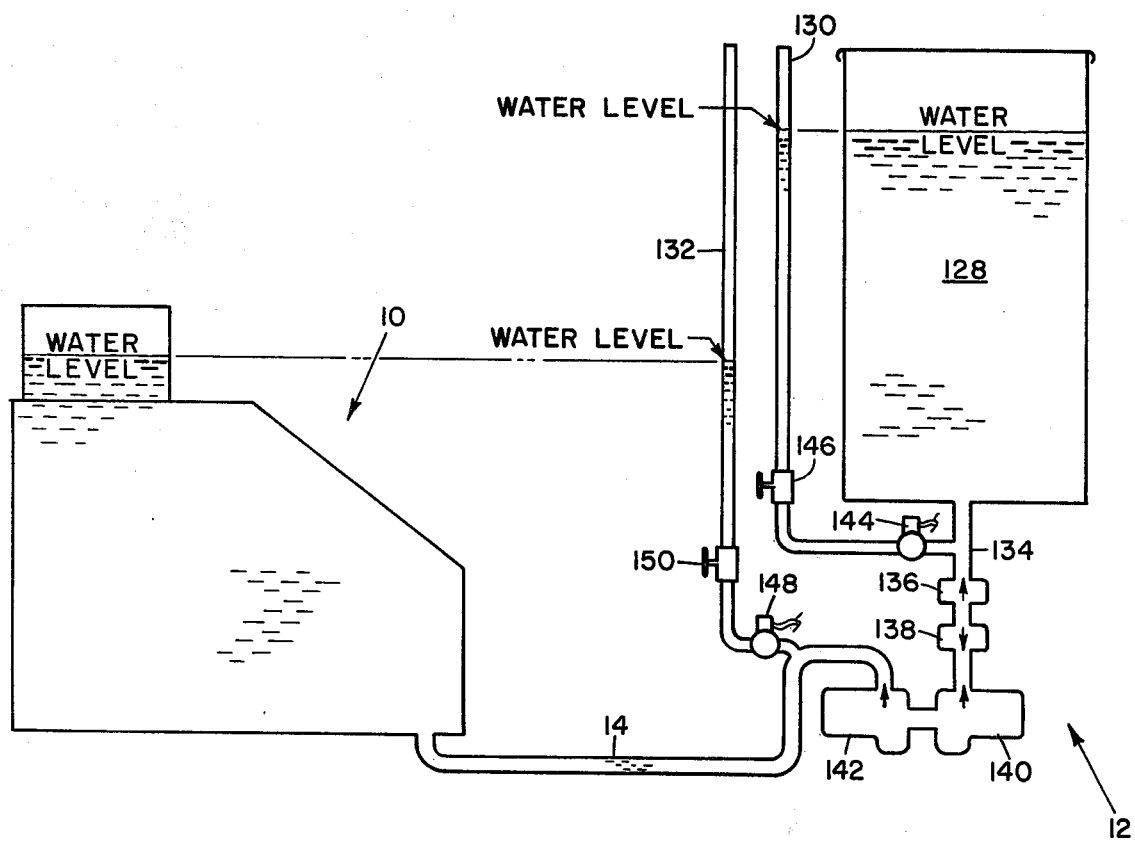
FIG. 8 is an illustrative elevated view showing internal connections of the control console.

Referring now to FIG. 8, operation of the lower control cabinet 124 is shown in more detail. Conduit 134 connects the tall cylinder 128 via back-to-back solenoid valves 136 and 138 to back-to-back pumps 140 and 142. Pumps 140 and 142 connect to tank 10 via flexible hose 14. Manometer 130 is connected to the tall cylinder 128 via conduit 134. Full open valve 144, which may be electrically or hand operated, is inserted between manometer 130 and conduit 134, as well as dampening valve 146. The purpose of the dampening valve 146 is to prevent oscillatory motion inside of the manometer 130. Dampening valve 146 may be a partially opened hand operated valve. Likewise, manometer 132 has a full open valve 148, which may be either electrically or hand operated, inserted prior to connection with flexible hose 14. Also, a dampening valve 150, which may again be a partially opened hand operated valve, prevents oscillatory motion of the water inside of manometer 132.

Referring to FIG. 1, located externally on the lower control cabinet 124 is a center off switch 152 which controls energization of pumps 140 and 142. As long as switch 152 is in the OFF position, neither pump 140 nor pump 142 is energized. Also, solenoid valves 136 and 138 remain closed preventing flow through conduit 134. By moving center off switch 152 to the "to tank" position, pump 142 is energized, and solenoid valves 136 and 138 are opened thereby causing fluid to be pumped from the tall cylinder 128 to the tank 10. Likewise, if switch 152 is changed to the opposite position of "from tank", pump 142 will be deenergized and pump 140 energized and water pumped from tank 10 to the tall cylinder 128. If either pump 140 or 142 is energized, solenoid valves 136 and 138 will remain open. If full open valves 144 and 148 are electrically operated, switch 154 will operate full open valve 144, and switch 156 will operate full open valve 148. The dampening valves 146 and 150 may be operated from any desired location on the control console, such as knobs 158 and 160, respectively. Full open valves 144 and 148 may be closed by switches 154 and 156, respectively, to allow sufficient time for a reading of manometers 130 or 132, respectively.

Figure 3:
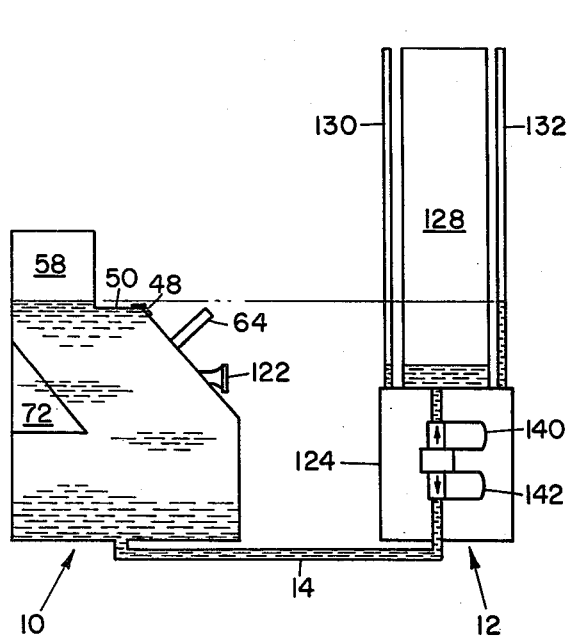
FIGS. 3, 4, 5 and 6 are pictorial sequential views illustrating use of the present invention.

Referring to FIGS. 3, 4, 5 and 6, a pictorial sequential view of the total body volume meter is shown. Referring first to FIG. 3, by closing lid 50, water is pumped from tall cylinder 128 into the tank 10 by pump 142 until the water begins to rise inside of transparent plastic cylinder 58. After turning OFF pump 142 and stablization of the water levels inside of manometers 130 and 132, the combined sum of the water levels inside of manometers 130 and 132 is recorded.

Figure 4:
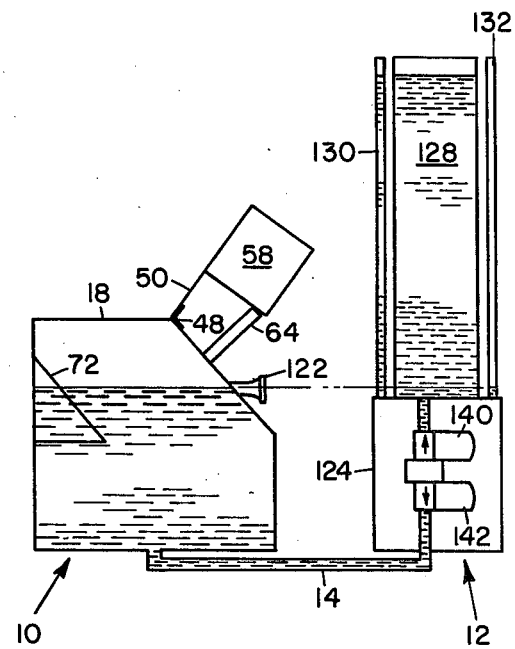

Thereafter, water is pumped by means of pump 140 from tank 10 back into tall cylinder 128 as shown in FIG. 4. Water remains inside of tank 10, but at a reduced level so that an individual may get inside of tank 10 through enlarged opening 18 without spilling water and sit on seat 72.

Figure 5:
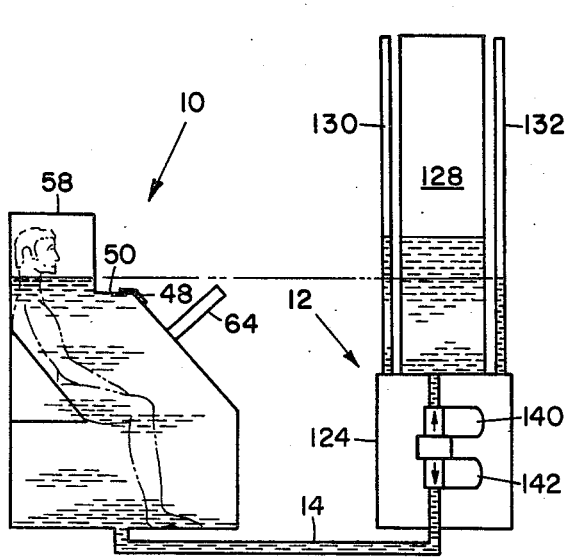

Referring now to FIG. 5, the individual enters the tank 10 through enlarged upper opening 18. The position of the seat 72 is adjusted so that the individual's head is located inside of the open ended transparent plastic cylinder 58. Pump 142 is then energized pumping water from tall cylinder 128 back into tank 10. When the water level has reached the individual's chin inside of transparent plastic cylinder 58, pump 142 is turned OFF.

Figure 6:
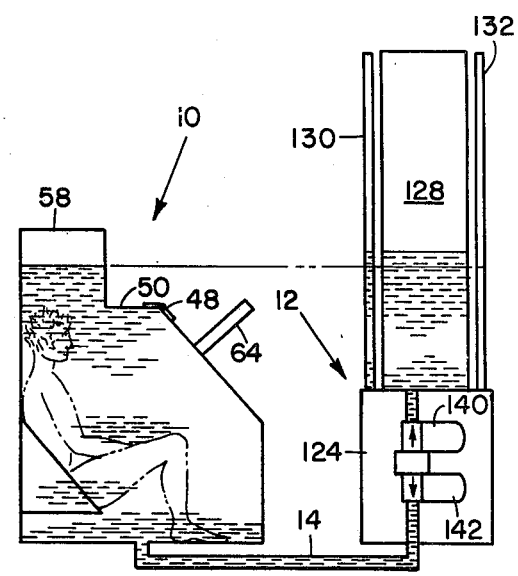

Referring to FIG. 6, by the individual inside of the tank 10 operating lever arm 112 (previously described in conjunction with FIGS. 2 and 7), seat 72 will lower and the individual will be immersed in the water contained in tank 10. Water level inside of the transparent plastic cylinder 58 will rise, as will the water level in manometer 132. The sum of the values shown on manometers 130 and 132 is then recorded. Because there may not be sufficient time to record the values of the water level in manometers 130 and 132 while an individual is immersed in the water, full open valves 144 and 148 may be closed by switches 154 and 156, respectively, upon stabilization of the water levels inside of the manometers 130 and 132. Thereafter, if the individual partially stands up, his head will raise above the water level inside of transparent plastic cylinder 58, and the seat 72 will rise to its previous level due to the float 78 (see FIG. 2). The individual can then rest his weight against seat 72 while the lid 50 is being opened.

By taking the difference between the sums recorded as described in conjunction with FIGS. 3 and 6, and multiplying that difference times the cross-sectional area of either transparent plastic cylinder 58 or tall cylinder 128 (which cross-sectional areas are the same), the total body volume of the individual is obtained.

By the use of the invention as just described, if the individual contained inside of the tank should have physical problems such as cardiac arrest, lid 50 can be quickly opened and the individual lifted upward. The water in tank 10 can be quickly removed by pump 140. The readings as obtained on the manometers are accurate in determining total body volume. By use of the thermometer 122, the temperature of the water can be controlled to approximately the same temperature as the human body. The present invention, as well as being simple in design, is very easy to use by physicians or therapists. Both the tank 10 and the control console 12 may be stored at any suitable location and simply rolled to the position where they will be used. All that is necessary is that both hot and cold water and a suitable electrical outlet be available at the place of usage. No hydraulic lifts, ladders, or sump wells are necessary.

I claim:

1. A total body volume meter for measuring body volume of an individual comprising:
   body tank means for holding a fluid therein, said body tank means having an enlarged upper opening for receiving said individual therethrough;
   uniform cross-sectional vertical tank means connected to said body tank means through conduit means;
   extension means of said enlarged upper opening, said extension means having a cross section approximately equal to said vertical tank means;
   a plurality of manometer means connected to said body tank means and said vertical tank means; and
   control means interconnected along said conduit means between said body tank means and said vertical tank means, levels of said fluid to be measured in said vertical tank means and said extension means by said manometer means before and after said individual enters said body tank means being adjusted by said control means.

2. The total body volume meter as given in claim 1 including lid means with said extension means mounted thereon, said lid means being adapted for sealing said enlarged upper opening except said extension means which is open ended.

3. The total body volume meter as given in claim 2 wherein said body tank means is constructed and arranged to receive said individual therein in a seated position on seat means inside said body tank means, said seat means being vertically moveable to lower said individual below said level of said fluid in said extension means.

4. The total body volume meter as given in claim 3 wherein said seat means is attached to one wall of said body tank means, vertical strap means positioned between said seat means and said wall, camming means pivotally carried by said seat means for rotatably engaging said strap means to prevent downward movement of said seat means, lever means carried by said seat means for rotatably releasing said camming means.

5. The total body volume meter as given in claim 2 wherein said control means includes pump means for pumping said fluid from said vertical tank means to said body tank means, valve means in said conduit means maintaining water levels in said body tank means and said vertical tank means during periods of nonuse of said pumping means.

6. The total body volume meter as given in claim 5 wherein said manometer means includes at least a first manometer connected to said vertical tank means and parallel therewith, and a second manometer connected to said body tank means and parallel with said extension means.

7. The total body volume meter as given in claim 6 wherein said extension means is a clear open ended cylinder and vertical tank means is a tall cylinder of equal diameter.

8. A method of measuring total body volume of an individual using a vertical tank of a given cross-sectional area and a body tank with an upper extension of said given cross-sectional area, said method consisting of the following steps:

filling said vertical tank with a substantial amount of a fluid and said body tank with said fluid until level of said fluid begins to raise in said upper extension;

first measuring heights of fluid levels in said vertical tank and said upper extension;

first recording a first sum of said first measured heights;

inserting said individual in said body tank and immersing said individual below said fluid level;

second measuring heights of said fluid levels in said vertical tank and said upper extension;

subtracting said first sum of said first measured heights from a second sum of said second measured heights to give a total height change of fluid levels; and expressing said cross-sectional area of the vertical tank together with said total height change of fluid levels in terms of total body volume of said individual.

9. The method as recited in claim 8 including after said first recording step an additional step of first pumping some of said fluid of said body tank into said vertical tank so that upon said immersing of said individual said level of said fluid is in said upper extension without spillage of said fluid.

10. The method as recited in claim 9 including a first step of sealing a lid means having said upper extension mounted thereon, after said first pumping step said lid means being unsealed and opened for said insertion of said individual therethrough and resealed.

11. The method as recited in claim 10 including after said resealing step a second pumping of said fluid from said vertical tank into said body tank until said fluid level reaches said upper extension.

12. The method as recited in claim 11 including final steps of removing at least some of said water from said body tank and second unsealing of said lid means for removal of said individual.

13. The method as recited in claim 8 wherein said individual is seated on a vertical moveable seat in said body tank, said immersing step including releasing said vertical moveable seat for said immersing of said individual.

14. The method as recited in claim 8 wherein said expressing step includes expressing said total body volume of the individual upon gauges.

* * * * *